United States Patent
Tuunanen

(10) Patent No.: US 6,197,597 B1
(45) Date of Patent: *Mar. 6, 2001

(54) SOLID PHASE IMMUNOASSAY WITH CARRIERS MATCHING THE SHAPE OF SAMPLE WELLS

(75) Inventor: Jukka Tuunanen, Helsinki (FI)

(73) Assignee: Labsystems Oy, Helsinki (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/495,515

(22) PCT Filed: Feb. 1, 1994

(86) PCT No.: PCT/FI94/00047

§ 371 Date: Aug. 29, 1995

§ 102(e) Date: Aug. 29, 1995

(87) PCT Pub. No.: WO94/18564

PCT Pub. Date: Aug. 18, 1994

(30) Foreign Application Priority Data

Feb. 1, 1993 (FI) .......................................... 930440

(51) Int. Cl.⁷ ................................................. G01N 33/533

(52) U.S. Cl. .......................... 436/518; 436/538; 436/807; 436/810; 436/824; 436/809; 435/7.1; 435/7.93; 435/287.9; 435/288.1; 435/294.1; 435/299.2; 435/305.3; 435/305.4; 435/962; 422/57; 422/58; 422/61; 422/63; 422/68.1; 422/99

(58) Field of Search .................... 422/57, 58, 61, 422/63, 68.1, 99; 435/7.1, 7.93, 7.94, 7.95, 287.9, 288.1, 288.4, 294.1, 299.2, 305.3, 305.4, 962; 436/518, 538, 807, 810, 824, 809

(56) References Cited

U.S. PATENT DOCUMENTS

| 2,471,764 | 5/1949 | Miller et al. ........................ 294/65.5 |
| 3,904,482 | * 9/1975 | Mehl .................................... 195/109 |
| 3,970,518 | 7/1976 | Giaever ................................ 195/1.5 |
| 3,985,649 | 10/1976 | Eddelman ............................. 210/42 |
| 4,018,886 | 4/1977 | Giaever ................................ 424/12 |
| 4,115,535 | 9/1978 | Giaever ................................ 424/1 |
| 4,197,287 | * 4/1980 | Piasio et al. . |

(List continued on next page.)

FOREIGN PATENT DOCUMENTS

| 2824742 A1 | * 2/1979 | (DE) . |
| 0 027 008 A1 | 4/1981 | (EP) ........................................ 33/54 |
| 0 042 755 A3 | 12/1981 | (EP) ........................................ 33/54 |
| 0186001 | * 7/1986 | (EP) . |
| 0317286 | 5/1989 | (EP) . |
| 0351857 | 1/1990 | (EP) . |
| 0358948 | 3/1990 | (EP) . |
| 0479448 A3 | 4/1992 | (EP) . |
| 0522322 A1 | 1/1993 | (EP) . |
| 1 414 479 | 11/1975 | (GB) ........................................ 33/16 |
| 2 147 698 | 10/1984 | (GB) ........................................ 33/543 |
| 2147 698 | 5/1985 | (GB) . |

(List continued on next page.)

Primary Examiner—Christopher L. Chin
Assistant Examiner—Bao-Thuy L. Nguyen
(74) Attorney, Agent, or Firm—Fish & Richardson, P.C.

(57) ABSTRACT

The invention concerns a solid-phase determination method and equipment and an adapter for use in these. In the method a sample is allowed to react with a separating reagent bound to the outer surface of a separate solid phase body, whereafter the body is removed from the vessel and is taken to a measurement vessel, if required through one or several intermediate step vessels. At least one vessel contains a medium needed in a determination step to be performed therein when the phase body is brought into this vessel. The invention is especially suitable for use in automatic immunodetermination systems.

17 Claims, 2 Drawing Sheets

U.S. PATENT DOCUMENTS

| | | | |
|---|---|---|---|
| 4,200,613 | 4/1980 | Alfrey et al. ........................... | 422/71 |
| 4,225,575 * | 9/1980 | Piasio et al. . | |
| 4,272,510 | 6/1981 | Smith et al. ........................... | 427/47 |
| 4,438,068 | 3/1984 | Forrest .................................. | 422/61 |
| 4,495,151 | 1/1985 | Ohyama et al. ...................... | 422/102 |
| 4,649,116 | 3/1987 | Daty et al. ............................ | 435/287 |
| 4,731,337 | 3/1988 | Hubscher .............................. | 435/293 |
| 4,751,053 | 6/1988 | Dodin et al. .......................... | 422/101 |
| 4,891,321 * | 1/1990 | Hubscher .............................. | 435/293 |
| 4,895,650 | 1/1990 | Wang .................................... | 210/222 |
| 5,167,926 | 12/1992 | Kimura et al. ........................ | 422/67 |
| 5,200,084 | 4/1993 | Liberti et al. ......................... | 210/695 |
| 5,206,034 | 4/1993 | Yamazaki .............................. | 425/145 |
| 5,318,914 | 6/1994 | Matte et al. ........................... | 436/526 |
| 5,466,574 | 11/1995 | Liberti et al. ......................... | 435/5 |
| 5,474,742 | 12/1995 | Tuuminen .............................. | 422/63 |
| 5,647,994 | 7/1997 | Tuunanen et al. ................... | 210/695 |

FOREIGN PATENT DOCUMENTS

| | | | |
|---|---|---|---|
| 63-5266 * | 2/1979 | (JP) . | |
| 58-5656 * | 1/1983 | (JP) . | |
| 58-5657 * | 1/1983 | (JP) . | |
| 58-5658 * | 1/1983 | (JP) . | |
| 63-5263 * | 1/1988 | (JP) . | |
| 63-5265 * | 1/1988 | (JP) ....................................... | 33/537 |
| WO 86/06493 | 11/1986 | (WO) . | |
| WO 87/05536 | 9/1987 | (WO) . | |
| WO 94/18564 | 8/1994 | (WO) . | |
| WO 94/18565 | 8/1994 | (WO) . | |
| WO 95/00247 | 1/1995 | (WO) . | |
| WO 9612958 | 5/1996 | (WO) . | |
| WO 9612959 | 5/1996 | (WO) . | |
| WO 9612960 | 5/1996 | (WO) . | |
| WO 9612961 | 5/1996 | (WO) . | |

* cited by examiner

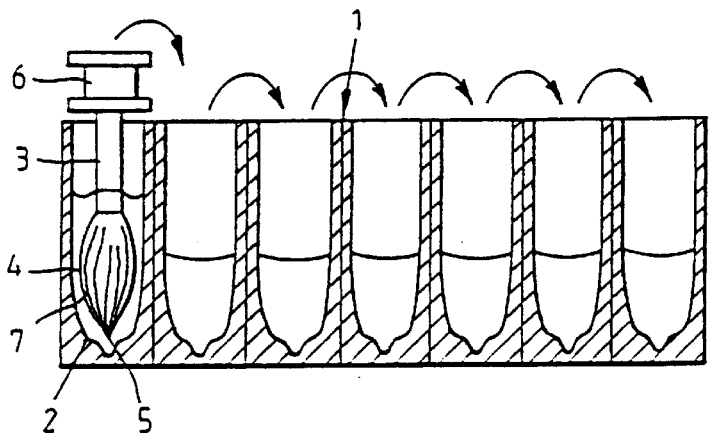
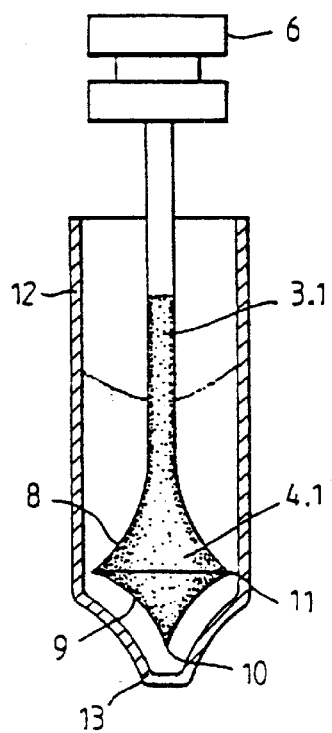
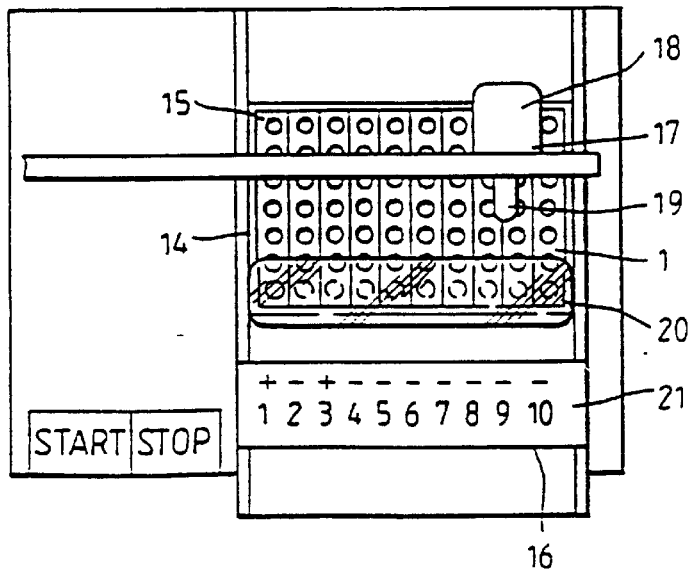

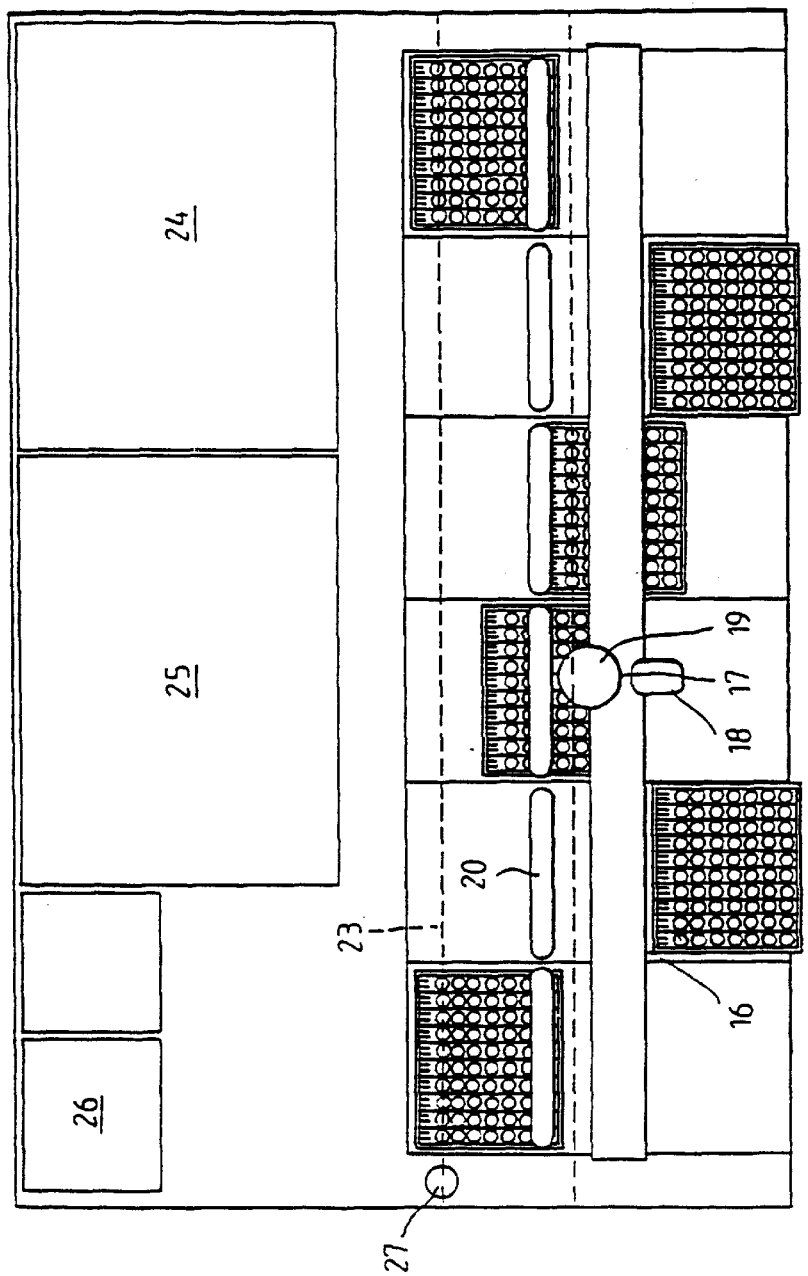
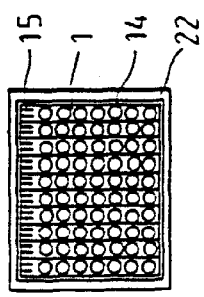
Fig. 4

SOLID PHASE IMMUNOASSAY WITH CARRIERS MATCHING THE SHAPE OF SAMPLE WELLS

FIELD OF THE INVENTION

The invention concerns a solid-phase determination method and equipment as well as an adapter for use in these. The invention is especially suitable for use in automatic immunodetermination systems.

BACKGROUND OF THE INVENTION

Solid-phase immunodetermination is usually carried out in one vessel so that the analyte to be determined in the sample is first allowed to react with a separating reagent bound in a solid phase, whereupon the other determination steps are carried out in the same vessel. The troublesome thing here is that you must do much dosing and removing of fluids. When there are several different determinations, a large stock of different reagents is also required.

Specification EP-A-194789 also presents a system, wherein the determination is carried out by using several vessels. The solid phase is formed by a thin strip which is moved from one vessel to another. The vessels contain the reagents needed in the determination method.

DESCRIPTION OF THE INVENTION

A determination method as defined in claim 1 has now been invented. Advantageous applications of the invention are defined in the following claims.

As used herein, a separating reagent generally means such a substance which will react with the analyte to be determined and will bind it in the solid phase. In immunodeterminations the separating reagent is usually an antigen or antibody. As used herein, a medium generally means a solution to be used at some stage of the determination, such as a reaction liquid or a washing fluid.

The solid phase used in the method is the outer surface of a solid body separate from the reaction vessel, and the determination steps are performed in two or more vessels. The solid-phase body is kept in the vessel containing the sample and the separating reaction is allowed to take place. Then intermediate steps, if such are required, are carried out in the other vessels and the phase body is finally moved over into the measuring vessel. Mediums needed in the determination are dosed beforehand into the vessels.

The phase body is of a cross-section similar to the reaction vessel, usually a circular one. In this way the diffusion distances from the solution to the solid phase will be as short as possible. In addition, the body can be used for efficient agitating of the reaction mixture.

The surface of the phase body is preferably of such a shape that fluid will flow off the surface as completely as possible. The best shape is oval with a tip at the bottom. However, the solid body may have, for example, several pins which are directed downwards. To enlarge the surface area, there may be suitable grooves or nodules on the body's surface. The reaction vessel bottom is preferably given the same shape as the phase body so that as little medium as possible will be required.

The vessels are preferably made as one unit. However, it is possible in principle to perform a-part of the steps outside the vessel unit, especially the measurement of the formed reaction product, should this be desirable. Using are outside measuring vessel could be suitable especially if the complex is observed directly from the solid phase, for example, fluoro-metrically or radiometrically.

Correspondingly, several steps may be performed in the same vessel, for example, washes. Medium may also be dosed into some vessel or removed from it. Using separate dosings might be suitable in those steps where exact dosing is not needed and where, for example, the same medium is used in several different determinations. Washes, in particular, could be such steps. However, in normal cases it is most advantageous to use such vessel units where all different mediums are ready in different vessels.

Washes at least are usually performed in intermediate determination steps. In addition, in intermediate steps the formed reaction complex is usually joined to a tracer which is then detected in the measuring step. The tracer may be either directly detectable or of such a type which will release some detectable compound, especially from a substrate. Detection usually takes place fluorometrically luminometrically, absorptiometrically or radiometrically.

There is no risk of contamination in the method, because the sample is not drawn into the equipment from the plate vessels. Besides, the method can be implemented by using simple and very reliably-operating automatic equipment. In addition, the phase body works as an effective agitating piston in the reaction vessel.

The invention is suitable, for example, for immunological, DNA-hybridization or hormone determinations.

The solid body is preferably in one piece. However, it may also be assembled into a separate frame from several parts, for example, rings.

To speed up mass transport and thus the necessary reaction time, the medium should be agitated during the reaction. This is preferably done by moving the phase body. It is especially advantageous to move the remover vertically, whereby the medium must flow through the gap between the remover and the vessel, thus blending very efficiently. To make mixing more effective, the body is constructed so wide that a gap of a suitable narrowness is formed between the vessel and the remover. Mixing can also be promoted by suitable designing of the body and the vessel.

The vessel unit forms a plate for use in one determination. The phase body may be packed into some vessel in the plate. The vessels to be used in the different steps may also be of different sizes.

The vessels are preferably closed with a film, which is punctured for carrying out the method. The film may be punctured by using the phase body, but using a separate puncturing point is recommended. The point may have cutting blades forming strips which will tear in a controlled manner. In the equipment, the puncturing point may be attached to the same actuator as the phase body. The top edge of the vessel is preferably provided with an extension against which the strips of the punctured film can rest. Closed vessels may have an inert gas phase to improve durability. The plate surface is preferably provided with a small gap between the vessels. This will reveal possible leaks under the film leading from one vessel to another.

The equipment may also have a safeguarding system which checks that there is medium in the vessel before the step is started. The phase body may function conveniently as the detector in such a system based on electrical conductivity measurement.

If desired, some suitable substance may be attached into that reaction vessel, into which the sample is brought, whereby the substance is attached to the vessel wall or to a separate solid phase remaining in the vessel. This substance will bind any such substances from the sample or from the formed complex that may disturb later determination steps.

The plate vessels are preferably in a single straight row, whereby you need to move the phase body only along a straight path in a horizontal plane in relation to the plate. The vessels of different steps may be located in any order in relation to each other. The vessels are preferably permanently fixed to one another. The plate may be made of some suitable material, preferably of plastic.

The plate is preferably provided with detent pins and the equipment with their counterparts, so that the plate can not be placed in a wrong position by mistake.

BRIEF DESCRIPTION OF DRAWINGS

In the following some embodiments of the invention are described by way of example. In the appended drawings FIG. 1 shows implementation of the method by using a solid-phase body, FIG. 2 shows an alternative solid-phase body, FIG. 3 shows equipment suitable for use when carrying out the method, and FIG. 4 shows another set of equipment of greater capacity.

According to FIG. 1, immunodetermination is performed by using a plate 1, which consists of seven wells 2 located in a straight row, and a rod 3 having a solid-phase body 4 and a separating reagent (e.g. an antibody) reacting with the analyte (for example, an antigen) to be determined and attached to the body surface.

The body 4 is oval and has a point 5 at its bottom end. The vessel 2 bottom is shaped correspondingly. At its upper end rod 3 has a handle 6 which is suitable for robotics and at which the rod can be grasped for exact control of its horizontal and vertical positions. The body surface has suitable protrusions and cavities 7 to increase the surface area. In this embodiment they are grooves leading toward the point.

The sample to be examined is brought first into the first well 2 in plate 1 containing a suitable diluter, if required, whereafter phase body 4 is immersed into it. The analyte possibly existing in the sample is now allowed to react with the separating reagent to form an immunocomplex. After this incubation the phase body is moved into the second well containing a first washing fluid, into the third well containing another washing fluid and into the fourth well containing an enzyme conjugate adhering to the immunocomplex. After tracer incubation the phase body is again moved by way of two washing wells for measurement in the last well containing a substrate for the enzyme, from which the enzyme will release a compound that can be detected fluorometrically. After the substrate reaction the phase body is taken aside and fluorometric measurement is performed in such a way that both excitation radiation and emission radiation are led through the well mouth.

During the incubations and washes the phase body is moved back and forth in a vessel, whereby the medium will blend effectively.

Plate 1 can be made of some cheap plastic material, because light need not be led through the well wall. For this reason, as simple a manufacturing technology as possible can also be used. To reduce background radiation the material is preferably opaque.

Luminometric determinations can be carried out in a similar way.

If the reaction result is measured absorptiometrically, the measuring vessel must be transparent or radiation must be provided through special arrangements (for example, using a reflecting bottom) from the measuring vessel to the detector.

No fluid transfers need to be done in the determination, whereby it is possible to construct a safe, simple and reliably-operating system.

In the device according to FIG. 2 there are a thin rod 3.1 and a solid-phase body 4.1 whose outer surface consists of two basically conical surfaces 8 and 9 curving inwardly. The rod diameter may be, for example, about one-tenth of the phase body diameter. Coating with the separating reagent should be done in such a way that also the rod is coated along its whole length coming into contact with the reaction solution. This is to prevent any unspecific reactions from taking place on the uncoated part. However, as the rod area is small compared to the phase body area, dosing exactitudes during the process will not have any strong effect on the treatment area of the coating.

The curved surfaces 8 and 9 of body 4.1 increase the surface area. The sharp point 10 and the sharp junction 11 of the surfaces make it easier for the fluid to flow off the body. The bottom 13 of vessel 12 is shaped to correspond with the body shape at its edges, but there is a level area in the middle.

Bodies consisting of several parts can be made for multiruns with the different parts coated with different reagents. For example, the body shown in FIG. 1 could consist of two vertical drop-halves, whereas the body shown in FIG. 2 could consist of two conical parts.

FIG. 3 shows a set of equipment where ten determinations can be performed at the same time.

Determination plates 1 are placed in a cassette 14. At the end of the last well in each plate there is a code 15 informing the equipment about the determination in question. The code can also give other information, especially the ageing time.

Cassette 14 is pushed into the equipment in the longitudinal direction of the plates with the code end first through opening 16, whereafter the cassette is moved automatically. The equipment has a detector end 17 movable in a transverse direction and provided with an identifying device 18 for reading the code and with a measuring device 19 for finding out the reaction result. Phase bodies and possible means for penetrating the film closures of the wells are placed on an arm 20. The equipment also includes a thermostatic heater for keeping the plates at the desired temperature.

A phase body is attached to arm 20 for each sample plate. Samples are dosed into the first well in the plates 1 in cassette 14 and the cassette is pushed in. It moves into its extreme position where identifying device 18 reads code 15, whereby a control unit receives the data needed for performing the determination. The phase bodies are lowered into the first wells. After incubation the phase bodies are taken up, the plate is moved one step forward and the second step is performed. The process goes on in this way from one well to another, and finally measuring is done in the last well. The determination result of each plate is shown on display 21.

All determinations may be different, provided that they can be performed with the number of wells available in the plate. All wells may not be needed in all determinations, in which case there is no medium in them.

Such equipment may of course also be used where both the detector end and the phase bodies are attached to the same arm.

FIG. 4 shows equipment of a modular type where six cassettes can be handled at the same time.

In this embodiment the available plates 1 have a code 15 at the end of the first well. Cassettes 14 are preheated in incubator 22 and they are pushed into the equipment with the code end first through feeding opening 16. The phase bodies needed for each cassette are located on arms 20 at the places of the corresponding plates.

The equipment has a common transversely movable detector end 17 provided with an identifying device 18 and with a measuring device 19. The identifying device reads code 15 in each plate, whereupon the cassette moves inward to its extreme position, wherein the sample and possibly deluting agent, too, are metered into the first well. Dashed line 23 shows the path of movement of the dosing device. The cassette is then moved outwardly so that the first well is located under phase body arm 20, and the first step is carried out. The cassette is then moved step by step inwardly, until the last well is located at the measuring device.

FIG. 4 also shows a diagrammatic view of energy-supplying unit 24, control unit 25, sample dosing pump 25, airing and diluter unit 26 and point washing well 27 in the equipment.

What is claimed is:

1. An apparatus for use in a solid-phase immunoassay to determine the presence of an analyte in a sample, the apparatus comprising:
   a. a reaction vessel for a sample to be analyzed;
   b. a solid phase body for insertion into a reaction vessel, said solid phase body having a cross-section similar to the reaction vessel, and an outer surface sloping continuously downwardly and having a sharp cusp at its lower end, the outer surface containing a separating reagent to react with the sample;
   c. at least one additional vessel for performing intermediate steps upon the solid phase body after the reaction between the separating reagent and the sample;
   d. a measuring vessel for conducting measurements of the reaction between the separating reagent and the sample in the measuring vessel; and
   e. an actuator means for inserting, removing, and moving the solid phase body from one vessel to another, wherein at least one vessel contains a medium when said solid phase body is inserted into said vessel.

2. The apparatus of claim 1 wherein the solid phase body has grooves or protrusions to increase the surface area of the solid phase body.

3. The apparatus of claim 1 wherein the solid phase body has grooves or ridges extending to its lowest end.

4. The apparatus of claim 1 further comprising an agitating means for agitating the medium in the vessel.

5. The apparatus of claim 4 wherein the agitating means is the solid phase body.

6. The apparatus of claim 5 wherein the solid phase body is moved vertically for agitating the medium.

7. The apparatus of claim 1 wherein each of the vessels contain medium.

8. The apparatus of claim 1 wherein each of the vessels are joined together to form one vessel unit.

9. The apparatus of claim 1 wherein at least one vessel is closed with a penetrable film.

10. The apparatus of claim 9 wherein each vessel is closed with a penetrable film.

11. The apparatus of claim 9 wherein at least one closed vessel contains an inert gas.

12. The apparatus of claim 1 in which said body is constructed of sufficient width to form a gap between a vessel and said removing means.

13. An apparatus for use in a solid-phase immunoassay to determine the presence of an analyte in a sample, the apparatus comprising:
   a. a reaction vessel for a sample to be analyzed;
   b. a solid phase body for insertion into a reaction vessel, said solid phase body having a cross-section similar to the reaction vessel, and having an outer surface sloping continuously downward and having a sharp cusp at its lowest end, the outer surface containing a separating reagent to react with the sample;
   c. at least one additional vessel for performing intermediate steps upon the solid phase body after the reaction between the separating reagent and the sample;
   d. a measuring vessel for conducting measurements of the reaction between the separating reagent and the sample;
   e. a measuring means for measuring the reaction between the separating reagent and the sample in the measuring vessel; and
   f. an actuator means for inserting, removing, and moving the solid phase body from one vessel to another, wherein at least one vessel contains a medium when said solid phase body is inserted into said vessel and said body being constructed of sufficient width to form a gap of suitable narrowness between a vessel and said removing means for moving said medium efficiently when said body is moved vertically in said vessel.

14. The apparatus of claim 13 in which said reaction vessel contains a medium and a substance is disposed within said medium.

15. An apparatus for use in a solid-phase immunoassay to determine the presence of an analyte in a sample, the apparatus comprising:
   a. a reaction vessel for a sample to be analyzed;
   b. a solid phase body for insertion into a reaction vessel, said solid phase body having a cross-section similar to the reaction vessel, and having an outer surface sloping continuously downward and having a sharp cusp at its lowest end, the outer surface containing a separating reagent to react with the sample;
   c. at least one additional vessel for performing intermediate steps upon the solid phase body after the reaction between the separating reagent and the sample;
   d. a measuring vessel for conducting measurements of the reaction between the separating reagent and the sample;
   e. a measuring means for measuring the reaction between the separating reagent and the sample in the measuring vessel; and
   f. an actuator means for inserting, removing, and moving the solid phase body from one vessel to another, wherein at least one vessel contains a medium when said phase body is inserted into said vessel, each of said vessels being joined together to form one vessel unit.

16. The apparatus of claim 15 in which said body is constructed of sufficient width to form a gap between a vessel and said removing means.

17. An apparatus for use in a solid-phase immunoassay to determine the presence of an analyte in a sample, the apparatus comprising:
   a. a solid phase body having an upper portion tapering outwardly from a smaller diameter to a maximum diameter, and a lower portion tapering inwardly from said maximum diameter, to a sharp cusp at a lower end of the lower portion, said upper portion and said lower portion defining an outer surface which contains a separating reagent; and
   b. a reaction vessel for the sample shaped complimentary to the lower portion of the solid phase body so that the lower portion of the solid phase body and the reaction vessel are in close proximity when the solid phase body is in the reaction vessel.

* * * * *